United States Patent [19]

Isak et al.

[11] Patent Number: 5,169,958
[45] Date of Patent: Dec. 8, 1992

[54] PREPARATION OF $\alpha,\beta$-UNSATURATED CARBONYL COMPOUNDS

[75] Inventors: Heinz Isak, Mutterstadt; Norbert Goetz, Worms; Thomas Kuekenhoehner, Frankenthal, all of Fed. Rep. of Germany

[73] Assignee: BASF Aktiengesellschaft, Ludwigshafen, Fed. Rep. of Germany

[21] Appl. No.: 769,022

[22] Filed: Oct. 1, 1991

[30] Foreign Application Priority Data

Oct. 6, 1990 [DE] Fed. Rep. of Germany ....... 4031723

[51] Int. Cl.$^5$ ................. C07D 307/02; C07C 69/76; C07C 45/00
[52] U.S. Cl. ................... 549/499; 549/498; 560/8; 560/55; 560/100; 560/104; 568/316; 568/436
[58] Field of Search .................. 560/104, 8; 568/316, 568/436; 549/498, 499

[56] References Cited

U.S. PATENT DOCUMENTS 4,624,969 11/1986 Keil et al. ........................... 71/88

FOREIGN PATENT DOCUMENTS 3437238 4/1986 Fed. Rep. of Germany .
3536117 4/1987 Fed. Rep. of Germany .

OTHER PUBLICATIONS

CA 109(10):85131k 1987.
CA 99(11):88241g 1983.
CA 81(19):120150t 1974.
J. Am. Chem. Soc. 71 (1949); 2671–2676.
Helv. Chim. Acta 52, (1969), 2465–2472.
Chem. Ber., (1958), 1359–1366.
C. R. Acda. Sci. C. 278 (1974) 1113–1116.

*Primary Examiner*—Paul J. Killos
*Attorney, Agent, or Firm*—Keil & Weinkauf

[57] ABSTRACT

A process for the preparation of $\alpha,\beta$-unsaturated carbonyl compounds of the formula I $$R^3-CH=\underset{\underset{R^2}{|}}{C}-\underset{\underset{O}{\|}}{C}-R^1 \quad (I)$$

where $R^1$ is hydrogen, $C_1$–$C_{10}$-alkyl, $C_1$–$C_{10}$-alkoxy or aryloxy, $R^2$ is aryl which is unsubstituted or substituted by $C_1$–$C_4$-alkyl, $C_1$–$C_4$-alkoxy, trifluoromethyl and/or halogen and $R^3$ is tetrahydrofuranyl or aryl which is substituted by $C_1$–$C_4$-alkyl, $C_1$–$C_4$-alkoxy, trifluoromethyl and/or halogen, which comprises reacting 3-amino-2-propen-1-ones of the formula II $$\underset{R^5}{\overset{R^4}{\diagdown}}N-CH=\underset{\underset{R^2}{|}}{C}-\underset{\underset{O}{\|}}{C}-R^1 \quad (II)$$

where $R^1$ and $R^2$ have the abovementioned meanings, and $R^4$ and $R^5$ are, independently of one another, hydrogen, $C_1$–$C_{10}$-alkyl or aryl, with a magnesium halide of the formula III $$R^3-Mg-Y \quad (III)$$

where Y is halogen, at from $-20°$ to $100°$ C., and novel $\alpha,\beta$-unsaturated carbonyl compounds and novel 3-amino-2-propen-1-ones are described.

9 Claims, No Drawings

PREPARATION OF α,β-UNSATURATED CARBONYL COMPOUNDS

The present invention relates to a novel process for the preparation of α,β-unsaturated carbonyl compounds and to novel 2-aminovinyl ketones.

J. Amer. Chem. Soc. 71 (1949), 2671–2676 discloses that methylmagnesium iodide reacts with dimethylaminomethylvinyl phenyl ketone in diethyl ether to give phenyl 1,2-dimethylvinyl ketone.

Helv. Chim. Acta 52, (1969), 2465–2472 and C. R. Acad. Sci. C. 278 (1974) 1113–1116 disclose the reaction of methylphenyl aminovinylalkyl ketone with alkyl halides to give unsaturated ketones in poor yields (20%).

Chem. Ber., (1958) 1359–1366 discloses that cinnamaldehyde is produced by reacting [N-methylanilino]2-propenal with phenylmagnesium bromide in 60% yield.

DE-A-34 37 238 and DE-A-35 36 117 disclose the preparation of α,β-unsaturated carbonyl compounds by condensation of aldehydes with ketones, specifically acetone, with base catalysis. This reaction resulted in mixtures of α,β- and β,γ-isomers which can be separated only with considerable effort.

It is an object of the present invention to remedy the abovementioned disadvantages.

We have found that this object is achieved by a novel and improved process for the preparation of α,β-unsaturated carbonyl compounds of the formula I

$$R^3-CH=C(R^2)-C(=O)-R^1 \quad (I)$$

where
R$^1$ is hydrogen, C$_1$–C$_{10}$-alkyl, C$_1$–C$_{10}$-alkoxy or aryloxy,
R$^2$ is aryl which is unsubstituted or substituted by C$_1$–C$_4$-alkyl, C$_1$–C$_4$-alkoxy, trifluoromethyl and/or halogen and
R$^3$ is tetrahydrofuranyl or aryl which is substituted by C$_1$–C$_4$-alkyl, C$_1$–C$_4$-alkoxy, trifluoromethyl and/or halogen,
which comprises reacting 3-amino-2-propen-1-ones of the formula II

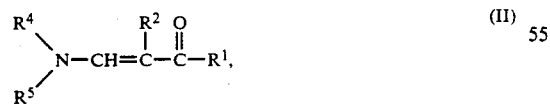

$$R^4R^5N-CH=C(R^2)-C(=O)-R^1 \quad (II)$$

where R$^1$ and R$^2$ have the abovementioned meanings, and R$^4$ and R$^5$ are, independently of one another, hydrogen, C$_1$–C$_{10}$-alkyl or aryl, with a magnesium halide of the formula III $$R^3-Mg-Y \quad (III),$$

where Y is halogen, at from $-20°$ to $100°$ C., as well as novel 3-amino-2-propen-1-ones of the formula II'

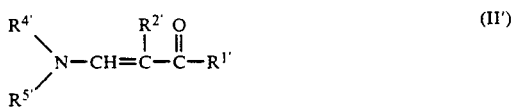

$$R^{4'}R^{5'}N-CH=C(R^{2'})-C(=O)-R^{1'} \quad (II')$$

where
R$^{1'}$ is hydrogen, C$_1$–C$_{10}$-alkyl, C$_1$–C$_{10}$-alkoxy or aryloxy,
R$^{2'}$ is aryl which is unsubstituted or substituted by C$_1$–C$_4$-alkyl, C$_1$–C$_4$-alkoxy, trifluoromethyl and/or halogen, and
R$^{4'}$, R$^{5'}$ are each C$_1$–C$_{10}$-alkyl,
with the proviso that R$^{1'}$ is not methyl when R$^{2'}$ is phenyl.

The process according to the invention can be carried out as follows:

A 3-amino-2-propen-1-ones of the formula II is added to a solution or suspension of a magnesium halide of the formula III at from $-20°$ to $100°$ C., preferably $-10°$ to $50°$ C., particularly preferably $0°-20°$ C.

The molar ratio of III to II is from 0.8:1 to 20:1, preferably 1:1 to 5:1, particularly preferably 1:1 to 1.2:1.

Suitable solvents are all solvents conventional for Grignard reactions, for example dipolar aprotic organic solvents, e.g. ethers such as diethyl ether, methyl tert-butyl ether, tetrahydrofuran, dioxane and dimethyl glycol ether; or amines such as triethylamine, or apolar aprotic organic solvents, eg. aliphatic hydrocarbons, such as cyclohexane, or aromatic hydrocarbons, such as benzene, toluene, mixed with dipolar aprotic solvents. Acyclic and cyclic ethers are preferred, such as diethyl ether, methyl tert-butyl ether, tetrahydrofuran, dioxane and dimethyl glycol ether, and cyclic ethers are particularly preferred, such as tetrahydrofuran and dioxane.

The solvents may contain water but preferably contain from 0 to 5% by weight of water, and are particularly preferably anhydrous.

Suitable magnesium halides of the formula III are the fluorides, chlorides, bromides and iodides, chlorides and bromides being preferred, and chlorides being particularly preferred.

The magnesium halides of the formula III can be prepared in a conventional manner by reacting the corresponding halides with magnesium in a solvent conventional for Grignard reactions.

The meanings of R$^1$, R$^2$, R$^3$, R$^4$ and R$^5$ in the compounds I, II and III are as follows:

R$^1$
hydrogen,
C$_1$–C$_{10}$-alkyl, preferably C$_1$–C$_8$-alkyl particularly preferably C$_1$–C$_4$-alkyl, such as methyl, ethyl, n-propyl, isopropyl, n-butyl, isobutyl, sec-butyl and tert-butyl,
C$_1$–C$_{10}$-alkoxy, preferably C$_1$–C$_8$-alkoxy, particularly preferably C$_1$–C$_4$-alkoxy, such as methoxy, ethoxy, n-propoxy, isopropoxy, n-butoxy, isobutoxy, sec-butoxy and tertbutoxy,
aryloxy, preferably phenoxy,
aryl such as phenyl, 1-naphthyl and 2-naphthyl, preferably phenyl,
aryl which is mono- to trisubstituted by C$_1$–C$_4$-alkyl, preferably phenyl which is mono- to trisubstituted by C$_1$–C$_4$-alkyl, such as 2-methylphenyl, 2,4-dimethylphenyl, 2,4-diisopropylphenyl and 2,4,6-trimethylphenyl, aryl which is mono- to trisubstituted by $C_1$–$C_4$-alkoxy, preferably phenyl which is mono- to trisubstituted by $C_1$–$C_4$-alkoxy, such as 2,4-dimethoxyphenyl, 4-methoxyphenyl, 2,4,6-trimethoxyphenyl, 2,4-diethoxyphenyl and 4-propyloxyphenyl, aryl which is mono- to trisubstituted by trifluoromethyl, preferably phenyl which is mono- to trisubstituted by trifluoromethyl such as 4-trifluoromethylphenyl, 3-chloro-4-trifluoromethylphenyl and 2-trifluoromethyl-4-methylphenyl, aryl which is mono- to trisubstituted by halogen, preferably phenyl which is mono- to trisubstituted by halogen, such as 2-chlorophenyl, 2,4-dichlorophenyl, 2-fluorophenyl, 2,4-difluorophenyl and 4-fluorophenyl, aryl which is mono- to trisubstituted by $C_1$–$C_4$-alkyl and $C_1$–$C_4$-alkoxy, preferably phenyl which mono- to trisubstituted by $C_1$–$C_4$-alkyl and $C_1$–$C_4$-alkoxy, such as 4-methoxy-2-isopropylphenyl, 2-methoxy-3-methylphenyl and 4-methoxy-2,6-dimethylphenyl, aryl which is mono- to trisubstituted by $C_1$–$C_4$-alkyl and trifluoromethyl, preferably phenyl which is mono- to trisubstituted by $C_1$–$C_4$-alkyl and trifluoromethyl, such as 4-trifluoromethyl-2-methylphenyl and 4-trifluoromethyl-2-isopropylphenyl, aryl which is mono- to trisubstituted by $C_1$–$C_4$-alkyl and halogen, preferably phenyl which is mono- to trisubstituted by $C_1$–$C_4$-alkyl and halogen, such as 2-methyl-4-chlorophenyl, 2-chloro-4-methylphenyl, 2-fluoro-4-methylphenyl and 2-methyl-4-fluorophenyl, aryl which is mono- to trisubstituted by $C_1$–$C_4$-alkoxy and trifluoromethyl, preferably phenyl which is mono- to trisubstituted by $C_1$–$C_4$-alkoxy and trifluoromethyl, such as 2,6-dimethoxy-4-trifluoromethylphenyl and 3-ethoxy-5-trifluoromethylphenyl, aryl which is mono- to trisubstituted by $C_1$–$C_4$-alkoxy and halogen, preferably phenyl which is mono- to trisubstituted by $C_1$–$C_4$-alkoxy and halogen, aryl which is mono- to trisubstituted by trifluoromethyl and halogen, preferably phenyl which is mono- to trisubstituted by trifluoromethyl and halogen, such as 2-fluoro-4-trifluoromethylphenyl and 2-chloro-4-trifluoromethylphenyl, $R^3$ tetrahydrofuranyl, aryl which is mono- to trisubstituted by $C_1$–$C_4$-alkyl, preferably phenyl which is mono-to trisubstituted by $C_1$–$C_4$-alkyl, such as 2-methylphenyl, 2,4-dimethylphenyl, 2,4-diisopropylphenyl and 2,4,6-trimethylphenyl, aryl which is mono- to trisubstituted by $C_1$–$C_4$-alkoxy, preferably phenyl which is mono- to trisubstituted by $C_1$–$C_4$-alkoxy, such as 2,4-dimethoxyphenyl, 2,4,6-trimethoxyphenyl and 2,4,6-triethoxyphenyl, aryl which is mono- to trisubstituted by trifluoromethyl, preferably phenyl which is mono- to trisubstituted by trifluoromethyl, such as 4-trifluoromethylphenyl and 2-chloro-4-trifluoromethylphenyl, aryl which is mono- to trisubstituted by halogen, preferably phenyl which is mono- to trisubstituted by halogen, such as 2-chlorophenyl, 2,4-dichlorophenyl, 2-fluorophenyl, 2,4-difluorophenyl and 4-fluorophenyl, aryl which is mono- to trisubstituted by $C_1$–$C_4$-alkyl and $C_1$–$C_2$-alkoxy, preferably phenyl which is mono- to trisubstituted by $C_1$–$C_4$-alkyl and $C_1$–$C_4$-alkoxy, such as 4-methoxy-2-isopropylphenyl, 2-methoxy-3-methylphenyl and 4-methoxy-2,6-dimethylphenyl, aryl which is mono- to trisubstituted by $C_1$–$C_4$-alkyl and trifluoromethyl, preferably phenyl which is mono- to trisubstituted by $C_1$–$C_4$-alkyl and trifluoromethyl, such as 4-trifluoromethyl-2-isopropylphenyl and 4-trifluoromethyl-2-methylphenyl, aryl which is mono- to trisubstituted by $C_1$–$C_4$-alkyl and halogen, preferably phenyl which is mono- to trisubstituted by $C_1$–$C_4$-alkyl and halogen, such as 2-methyl-4-chlorophenyl, 2-chloro-4-methylphenyl, 2-fluoro-4-methylphenyl and 2-methyl-4-fluorophenyl, aryl which is mono- to trisubstituted by $C_1$–$C_4$-alkoxy and trifluoromethyl, preferably phenyl which is mono- to trisubstituted by $C_1$–$C_4$-alkoxy and trifluoromethyl, such as 2-methoxy-4-trifluoromethylphenyl and 2,6-dimethoxy-4-trifluoromethylphenyl, aryl which is mono- to trisubstituted by $C_1$–$C_4$-alkoxy and halogen, preferably phenyl which is mono- to trisubstituted by $C_1$–$C_4$-alkoxy and halogen, such as 2,6-dichloro-4-ethoxyphenyl and 2-chloro-4-methoxyphenyl and 2-fluoro-4-methoxyphenyl, aryl which is mono- to trisubstituted by trifluoromethyl and halogen, preferably phenyl which is mono- to trisubstituted by trifluoromethyl and halogen, such as 2-fluoro-4-trifluoromethylphenyl, 2,6-dichloro-4-trifluoromethylphenyl and 4-chloro-2-trifluoromethylphenyl, $R^4$, $R^5$ independently of one another hydrogen, $C_1$–$C_{10}$-alkyl, preferably $C_1$–$C_8$-alkyl, particularly preferably $C_1$–$C_4$-alkyl, such as methyl, ethyl, n-propyl, isopropyl, n-butyl, isobutyl, sec-butyl and tert-butyl, aryl such as phenyl.

Examples of compounds I which can be prepared by the novel process are:

2-phenyl-2-buten-1-al
2-(4-chlorophenyl)-2-buten-1-al
2-(2,4-dichlorophenyl)-2-buten-1-al
2-(2-methylphenyl)-3-penten-2-one
2-(2,4-dichlorophenyl)-3-penten-2-one
2-(4-trifluoromethylphenyl)-3-penten-2-one
Methyl 2-(2-methylphenyl)-2-butenoate
Methyl 2-(2,4-dichlorophenyl)-2-butenoate
Ethyl 2-(2,4-methylphenyl)-2-butenoate
Ethyl 2-(2,4-dichlorophenyl)-2-butenoate
Propyl 2-(2-chlorophenyl)-2-butenoate
2-ethylidenecyclohexan-1-one
2-ethylidene-6-methylcyclohexan-1-one
2-isopropylidenecyclohexan-1-one
2-(4-fluorophenyl)-3-(2,4-dimethylphenyl)acrolein
2-phenyl-3-(4-methylphenyl)acrolein
2-phenyl-3-(3,4-dichlorophenyl)acrolein
2-phenyl-3-(2,4-dichlorophenyl)acrolein
2-phenyl-3-(2,4,6-trichlorophenyl)acrolein
2-phenyl-3-(2,4,6-trimethylphenyl)acrolein
2-phenyl-3-(3,4,5-trichlorophenyl)acrolein
2-(4-fluorophenyl)-3-(2-methylphenyl)acrolein
2-phenyl-3-(2-trifluoromethylphenyl)acrolein
2-(4-chlorophenyl)-3-(2-methoxyphenyl)acrolein
2-(4-fluorophenyl)-3-(4-trifluoromethylphenyl)acrolein 2-(4-bromophenyl)-3-(4-chlorophenyl)acrolein The substituents $R^{1'}$, $R^{2'}$, $R^{4'}$ and $R^{5'}$ in compounds II' have the following meanings:

$R^{1'}$
hydrogen,
$C_1$-$C_{10}$-alkyl, preferably $C_1$-$C_8$-alkyl, particularly preferably $C_1$-$C_4$-alkyl, such as methyl, ethyl, n-propyl, isopropyl, n-butyl, isobutyl, sec-butyl and tert-butyl,
$C_1$-$C_{10}$-alkoxy, preferably $C_1$-$C_8$-alkoxy, particularly preferably $C_1$-$C_4$-alkoxy, such as methoxy, ethoxy, n-propoxy, isopropoxy, n-butoxy, isobutoxy, sec-butoxy and tertbutoxy,
aryloxy, preferably phenoxy, $R^{2'}$
aryl such as phenyl, 1-naphthyl and 2-naphthyl, preferably phenyl,
aryl which is mono- to trisubstituted by $C_1$-$C_4$-alkyl, preferably phenyl which is mono- to trisubstituted by $C_1$-$C_4$-alkyl, such as 2-methylphenyl, 2,4-dimethylphenyl, 2,4-diisopropylphenyl and 2,4,6-trimethylphenyl,
aryl which is mono- to trisubstituted by $C_1$-$C_4$-alkoxy, preferably phenyl which is mono- to trisubstituted by $C_1$-$C_4$-alkoxy, such as 2,4-dimethoxyphenyl, 4-methoxyphenyl, 2,4,6-trimethoxyphenyl, 2,4-diethoxyphenyl and 4-propyloxyphenyl,
aryl which is mono- to trisubstituted by trifluoromethyl, preferably phenyl which is mono- to trisubstituted by trifluoromethyl, such as 4-trifluoromethylphenyl, 3-chloro-4-trifluoromethylphenyl and 2-trifluoromethyl-4-methylphenyl,
aryl which is mono- to trisubstituted by halogen, preferably phenyl which is mono- to trisubstituted by halogen, such as 2-chlorophenyl, 2,4-dichlorophenyl, 2-fluorophenyl, 2,4-difluorophenyl and 4-fluorophenyl,
aryl which is mono- to trisubstituted by $C_1$-$C_4$-alkyl and $C_1$-$C_4$-alkoxy, preferably phenyl which is mono- to trisubstituted by $C_1$-$C_4$-alkyl and $C_1$-$C_4$-alkoxy, such as 4-methoxy-2-isopropylphenyl, 2-methoxy-3-methylphenyl and 4-methoxy-2,6-dimethylphenyl,
aryl which is mono- to trisubstituted by $C_1$-$C_4$-alkyl and trifluoromethyl, preferably phenyl which is mono- to trisubstituted by $C_1$-$C_4$-alkyl and trifluoromethyl, such as 4-trifluoromethyl-2-methylphenyl and 4-trifluoromethyl-2-isopropylphenyl,
aryl which is mono- to trisubstituted by $C_1$-$C_4$-alkyl and halogen, preferably phenyl which is mono- to trisubstituted by $C_1$-$C_4$-alkyl and halogen, such as 2-methyl-4-chlorophenyl, 2-chloro-4-methylphenyl, 2-fluoro-4-methylphenyl and 2-methyl-4-fluorophenyl,
aryl which is mono- to trisubstituted by $C_1$-$C_4$-alkoxy and trifluoromethyl, preferably phenyl which is mono- to trisubstituted by $C_1$-$C_4$-alkoxy and trifluoromethyl, such as 2,6-dimethoxy-4-trifluoromethylphenyl and 3-ethoxy-5-trifluoromethylphenyl,
aryl which is mono- to trisubstituted by $C_1$-$C_{14}$-alkoxy and halogen, preferably phenyl which is mono- to trisubstituted by $C_1$-$C_4$-alkoxy and halogen,
aryl which is mono- to trisubstituted by trifluoromethyl and halogen, preferably phenyl which is mono- to trisubstituted by trifluoromethyl and halogen, such as 2-fluoro-4-trifluoromethylphenyl and 2-chloro-4-trifluoromethylphenyl, $R^{4'}$, $R^{5'}$
independently of one another
hydrogen,
$C_1$-$C_{10}$-alkyl, preferably $C_1$-$C_8$-alkyl, particularly preferably $C_1$-$C_4$-alkyl, such as methyl, ethyl, n-propyl, isopropyl, n-butyl, isobutyl, sec-butyl and tert-butyl,
aryloxy, preferably phenoxy.

The following are particularly preferred novel compounds II':

| $R^{1'}$ | $R^{2'}$ | $R^{4'}$ | $R^{5'}$ |
|---|---|---|---|
| hydrogen | phenyl | methyl | methyl |
| methyl | 2-methylphenyl | methyl | methyl |
| methoxy | 2-methylphenyl | methyl | methyl |
| hydrogen | 4-fluorophenyl | methyl | methyl |
| hydrogen | 4-chlorophenyl | methyl | methyl |

The compounds I which can be prepared by the process according to the invention, and the novel compounds I' are suitable as intermediates for active ingredients in crop protection agents (DE-A-34 37 238, DE-A-35 36 117 and DE-A-36 01 066).

EXAMPLES

Example 1

Preparation of 3-phenyl-2-buten-1-al

3-Dimethylamino-3-phenyl-2-propen-1-al in 500 ml of tetrahydrofuran is added over the course of 3 hours to 2.16 mol of a 1.5 molar solution of methylmagnesium chloride in tetrahydrofuran which is kept at 15°-20° C. by cooling. The mixture is then stirred into 3 liters of a saturated NH$_4$Cl solution and dissolved by adding water. Phase separation and fractional distillation result in 210 g (93%) of 3-phenyl-2-buten-1-al of boiling point 80°-90° C. under 0.35 torr.

The compounds listed in the following table were prepared in a similar manner to Example 1:

TABLE

| Compound No. | $R^1$ | $R^2$ | $R^3$ | Boiling point [°C.] | Melting point [°C./mbar] |
|---|---|---|---|---|---|
| 2 | H | 4-fluorophenyl | 2,4-dimethylphenyl | 135/0.1 | — |
| 3 | H | phenyl | 4-methylphenyl | 134/0.2 | — |
| 4 | H | phenyl | 3,4-dichlorophenyl | — | 124 |
| 5 | H | phenyl | 2,4-dichlorophenyl | — | 98 |
| 6 | H | phenyl | 2,4,6-trimethylphenyl | — | 110 |
| 7 | H | phenyl | 3,4,5-trichlorophenyl | — | 165 |
| 8 | H | 4-fluorophenyl | 2-methylphenyl | 135/0.3 | 75 |
| 9 | H | phenyl | 2-trifluoromethylphenyl | — | 64 |
| 10 | H | 4-chlorophenyl | 2-methoxyphenyl | 175/0.4 | — |
| 11 | H | 4-fluorophenyl | 4-trifluoromethylphenyl | 142/0.25 | 86 |

We claim:

1. A process for the preparation of $\alpha,\beta$-unsaturated carbonyl compounds of the formula I

(I)

where
- R$^1$ is hydrogen, C-C$_{10}$-alkyl, C$_1$-C$_{10}$-alkoxy or aryloxy,
- R$^2$ is aryl which is unsubstituted or substituted by C$_1$-C$_4$-alkyl, C$_1$-C$_4$-alkoxy, trifluoromethyl and/or halogen and
- R$^3$ is tetrahydrofuranyl or aryl which is substituted by C$_1$-C$_4$-alkyl, C$_1$-C$_4$-alkoxy, trifluoromethyl and/or halogen, which comprises reacting 3-amino-2-propen-1-ones of the formula II

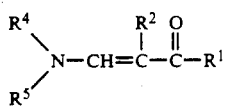 (II)

where R$^1$ and R$^2$ have the abovementioned meanings, and R$^4$ and R$^5$ are, independently of one another, hydrogen, C$_1$-C$_{10}$-alkyl or aryl, with a magnesium halide of the formula III

 (III), where Y is halogen, at from $-20°$ to $100°$ C., in a molar ratio of compound III to compound II of from 0.8:1 to 20:1 and at a temperature of from $-20°$ to $100°$ C.

2. The process of claim 1, wherein a compound of the formula II is added to a solution or suspension of a compound of the formula III.

3. The process of claim 1, wherein the reaction temperature is from $-10°$ to $50°$ C.

4. The process of claim 1, wherein the reaction temperature is from $0°$ to $20°$ C.

5. The process of claim 1, wherein the ratio of compound III to compound II is from 1:1 to 5:1.

6. The process of claim 1, wherein the ratio of compound III to compound II is from 1:1 to 1.2:1.

7. The process of claim 1, wherein a compound of the formula II is added to a solution of a compound of the formula III.

8. The process of claim 7, wherein the solvent is a dipolar aprotic organic solvent.

9. The process of claim 7, wherein the solvent is tetrahydrofuran or dioxane, the temperature is from $0°$ to $20°$ C. and the ratio of compound III to compound II is from 1:1 to 5:1.

* * * * *

UNITED STATES PATENT AND TRADEMARK OFFICE
CERTIFICATE OF CORRECTION

PATENT NO. : 5,169,958

DATED : December 8, 1992

INVENTOR(S) : ISAK et al.

It is certified that error appears in the above-identified patent and that said Letters Patent is hereby corrected as shown below:

Claim 1, column 7, line 2: "$C-C_{10}$-alkyl" should read -- $C_1-C_{10}$-alkyl --

Signed and Sealed this

Sixteenth Day of November, 1993

Attest:

BRUCE LEHMAN

Attesting Officer

*Commissioner of Patents and Trademarks*